United States Patent

Matsuura et al.

[11] Patent Number: 5,929,347
[45] Date of Patent: Jul. 27, 1999

[54] APPARATUS FOR SAMPLING DUST IN A DUCT

[75] Inventors: Kenji Matsuura, Osaka; Junichi Shiraishi, Hyogo, both of Japan

[73] Assignees: Ataka Construction & Engineering; Kobe Mechatronics Co., Ltd., both of Japan

[21] Appl. No.: 08/809,545
[22] PCT Filed: Mar. 15, 1996
[86] PCT No.: PCT/JP96/00714
§ 371 Date: Mar. 21, 1997
§ 102(e) Date: Mar. 21, 1997
[87] PCT Pub. No.: WO97/22868
PCT Pub. Date: Jun. 26, 1997

[30] Foreign Application Priority Data

Dec. 15, 1995 [JP] Japan .................................. 7-348075

[51] Int. Cl.⁶ .............................. G01N 1/04; G01N 1/08
[52] U.S. Cl. .................................... 73/863.01; 73/864.31; 73/864.41
[58] Field of Search .......................... 73/863.01, 864.31, 73/864.32, 864.33, 864.41

[56] References Cited

U.S. PATENT DOCUMENTS

| 3,677,427 | 7/1972 | Allen | 214/140 |
|---|---|---|---|
| 4,177,624 | 12/1979 | Kelpin | 56/9 |
| 4,304,139 | 12/1981 | Johnson | 73/864.32 |
| 4,558,602 | 12/1985 | Redding | 73/863.01 X |
| 4,763,376 | 8/1988 | Spurlock, Jr. et al. | 15/104.31 |
| 5,311,641 | 5/1994 | Metsuure et al. | 15/406 |
| 5,317,782 | 6/1994 | Matsuura et al. | 15/324 |
| 5,333,533 | 8/1994 | Hosseini | 91/361 |
| 5,392,659 | 2/1995 | Ford, Jr. et al. | 73/863.01 X |
| 5,572,706 | 11/1996 | Metsuura et al. | 15/304 |

FOREIGN PATENT DOCUMENTS

| 2693220 | 1/1994 | France . |
|---|---|---|
| 2236572 | 4/1991 | United Kingdom . |

OTHER PUBLICATIONS

Patent Abstracts of Europe (FR 02693220 A1) dated Jan. 7, 1994 inventor Jean "Remote Controlled Hydraulically Powered Sewer Cleaning Method–Uses Tracked Vehicle with Front Mounted Cutter/Grinder and Outlet Pipe Discharging Into Barge with Data Collectors Mounted on Front Above".

*Primary Examiner*—Thomas P. Noland
*Attorney, Agent, or Firm*—Edwin E. Greigg; Ronald E. Greigg

[57] ABSTRACT

An apparatus for sampling dust in a duct for the purpose of knowing, in advance a need for cleaning the inside of such a narrow duct as can not be accessed internally by a person, the kinds of accumulations in the duct and the state of accumulation and sticking or the like. The apparatus comprises a traveling truck enabled to travel forwardly and backwardly in the duct, a TV camera mounted on the traveling truck in order to observe the inside of the duct, a sampling bucket attached to the front of the traveling truck in order to sample accumulations in the duct and a remote control portion for remotely controlling the traveling truck, the TV camera and the sampling bucket.

1 Claim, 6 Drawing Sheets

APPARATUS FOR SAMPLING DUST IN A DUCT

RELATED PATENTS

The present application relates to the following patents, U.S. Pat. Nos. 5,311,641, 5,317,782 and 5,572,766.

TECHNOLOGICAL FIELD

The present invention relates to an apparatus for sampling dust and other dirt accumulations in a duct while traveling therein, to examine the kinds and properties of the sampled material, the apparatus must be enabled to travel in a narrow duct with a small inner diameter such as 150 mm.

BACKGROUND ART

Such narrow ducts which can not be internally accessed by a person have had their inside cleaned by a small-sized cleaning apparatus traveling therein. The apparatus comprises a traveling truck equipped with means for removing dust and contaminations accumulated on or adhering to the inner surface of the duct. Such small-sized duct cleaning apparatus may, however, be said to be still under development. In addition, attention has been paid principally to the technology of effectively discharging dust and contaminations from a duct; but it has not been taken into account to examine, in advance, the kinds, properties, state of accumulation and adhesion of the dust in a duct to be cleaned.

Recently, however, the dust and dirt accumulations in a duct have widely come to have their type, properties and state of accumulation and sticking diversified. In some cases very specific foreign substances are found sticking and accumulating. Therefore, to clean the inside of a duct effectively it is important to grasp, in advance, the types, features and state of sticking and accumulation of foreign matters in a duct both quantitatively and qualitatively. However, the apparatus for examining the properties of the contaminations in a narrow duct has not been sufficiently developed so far.

The applicant of the present patent application provided an apparatus for searching in a duct both in Japanese Patent Application No. 4-220683 and in the U.S. Pat. No. 5,311,641, but the apparatus has no function of dust sampling.

Accordingly, the present invention aims at eliminating such a disadvantage in the conventional technology and makes it an object to provide an apparatus for sampling dust in a duct to grasp the types, properties, state of accumulation and sticking of the contaminations in the duct in advance of cleaning the duct.

DISCLOSURE OF INVENTION

To achieve the above object, the apparatus for sampling dust in a duct, in accordance with the present invention, comprises essentially a traveling truck capable of traveling forwardly and backwardly in a duct, an illuminating light is mounted on a front end of the traveling truck for illuminating the inside surface of the duct, a TV camera is mounted on the front end of the traveling truck for observing the inside surface of the duct, at least one compressed air ejection nozzle is mounted on the front end of the traveling truck for ejecting compressed air toward any accumulation in the duct in front of the traveling truck, a sampling bucket means, mounted on a front end of the traveling truck and movable about a shaft between a lower position for scooping-up accumulations in the duct and an upper position in a standby position without blocking a view of the TV camera and the compressed air ejected from behind the sampling bucket. The movement of the travel truck and operation of the illuminating light, the TV camera, the compressed air and the sampling bucket means are all operated remotely by an operator that monitors an inside of the duct via a TV screen which shows the subject matter viewed by the TV camera, - - - .

The bucket means of the apparatus comprises a shaft supported by and between a pair of supporting elements that project forwardly from the front part of the traveling truck, a pair of rotation arms supported by said shaft and rotatable around said shaft, an air cylinder for making said pair of rotation arms turn between a standby position and a scooping position, a hydraulic damper for damping the turning speed of the rotation arms made to turn by said air cylinder, and a sampling bucket detachably attached to and between said pair of rotation arms.

According to the first feature of the present invention an operator of the apparatus can, by operating the remote control portion, observe the situation inside a duct through the TV camera mounted on the traveling truck while making the same travel in the duct. When the traveling truck comes to a place where dust sampling seems necessary, the operator can sample dust accumulations by manipulating the bucket means through the operation of the remote control portion. With the sampling finished the traveling truck is returned to the entrance of the duct, and the the sampled dust accumulations are removed for analysis.

According to the above first feature the apparatus of the present invention comprises a traveling truck capable of traveling freely in a duct if put therein, a TV camera mounted on the traveling truck to observe the inside view of the duct, bucket means attached to the head portion of the traveling truck to sample acumulations in the duct, and a remote control portion for remotely controlling said traveling truck, said TV camera and said bucket means.

Therefore, an operator of the apparatus can, by means of remote control, observe the situation inside a duct through the TV camera mounted on the traveling truck by making the traveling truck travel in such a narrow duct that can not be accessed internally by a person, and further the operator can remotely control the bucket means so as to sample accumulations in the duct where dust sampling seems necessary. After the sampling, the traveling truck can be returned to the entrance of the duct, and the sampled accumulations are taken out for analysis.

According to the above second feature of the present invention, in addition to the working in accordance with the above first feature, an operator of the apparatus can make an observation by means of the TV camera while making the traveling truck travel in a duct and blow off accumulations, as occasion demands, by making compressed air spout from the compressed air ejection nozzle mounted on the traveling truck. Further the operator can not only observe the state of blowing but also sample with the bucket means the accumulations remaining which are not blown off. The sampled accumulations are offered for analysis. Besides, the duct can also be cleaned, after the completion of sampling, by blowing off the accumulations in the duct by the use of the compressd air ejection nozzle.

According to the above second feature the apparatus of the present invention has its traveling truck provided with the compressed air ejection nozzle capable of spouting compressed air to the accumulations in front of the traveling truck in a duct by being remotely controlled through the remote control portion.

Therefore, in addition to the working and effect due to the first feature, an operator of the apparatus can make an observation by means of the TV camera while making the traveling truck travel in a duct and blow off accumulations, as an occasion demands, by making compressed air spout from the compressed air ejection nozzle mounted on the traveling truck. Further the operator can not only observe the state of blowing but also sample with the bucket means the accumulations remaining without being blown off. The sampled accumulations are offered for analysis. Besides, the duct can also be cleaned, after the completion of sampling, by blowing off the accumulations in the duct by the use of the compressed air ejection nozzle.

According to the above third feature of the present invention, in addition to the working in accordance with the above second feature, an operator of the apparatus puts the traveling truck into a duct with the sampling bucket attached to the pair of the rotation arms of the traveling truck, makes the traveling truck travel in the duct with the sampling duct kept at the standby position by remotely operating the air cylinder, and observes the inside of the duct through the TV camera. Then the operator remotely operates the air cylinder, at a place where dust sampling seems necessary, so as to move the sampling bucket from the standby position to the scooping position. Preparation to sample accumulations in the duct thus comes to be completed. Thus it is possible to sample accumulations in the duct by means of scooping. The combination of the air cylinder with the hydraulic damper makes it possible for the hydraulic damper to moderately deaden the shocks that may happen on the rotation arms when they are made to start turning or are kept in the process of turning or are made to stop by the air cylinder. The scooped matter can thus be prevented from spilling out of the bucket.

According to the above third feature the apparatus of the present invention has its bucket means composed of a shaft supported by and between a pair of supporting elements projecting forwardly from the front part of the traveling truck, a pair of rotation arms supported by said shaft rotatably around the same, an air cylinder for making said pair of rotation arms turn between a standby position and a scooping position, a hydraulic damper for deadening the turning speed of the rotation arms made to turn by said air cylinder, and a sampling bucket detachably attached to and between said pair of rotation arms.

Therefore, in addition to the effects resulting from the make-up of the apparatus, an operator of the apparatus can easily turn the sampling bucket to the scooping position from the sandby position and can easily return the same to the original standby position after sampling, since the air cylinder, the rotation arms and the sampling bucket are functionally combined. This not only causes easy sampling but also makes it easy for the traveling truck to move when sampling is not carried out. Further, possible malfunctions of other constituent elements can easily be avoided. The combination of the air cylinder with the hydraulic damper makes it possible for the hydraulic damper to moderately deaden the shocks that may happen on the rotation arms when they are made to start turning or are kept in the process of turning or are made to stop by the air cylinder. The scooped matter can thus be prevented from spilling out of the bucket.

BRIEF DESCRIPTION OF DRAWINGS

FIGS. 7A and 7B show perspective views of two sampling buckets: FIG. 7(A) one has a flat scooping plate, and FIG. 7(B) has a somewhat warped scooping plate.

BEST MODE FOR CARRYING OUT THE INVENTION

In the following the present invention is described in detail in accordance with the accompanying drawings.

Figure 1:
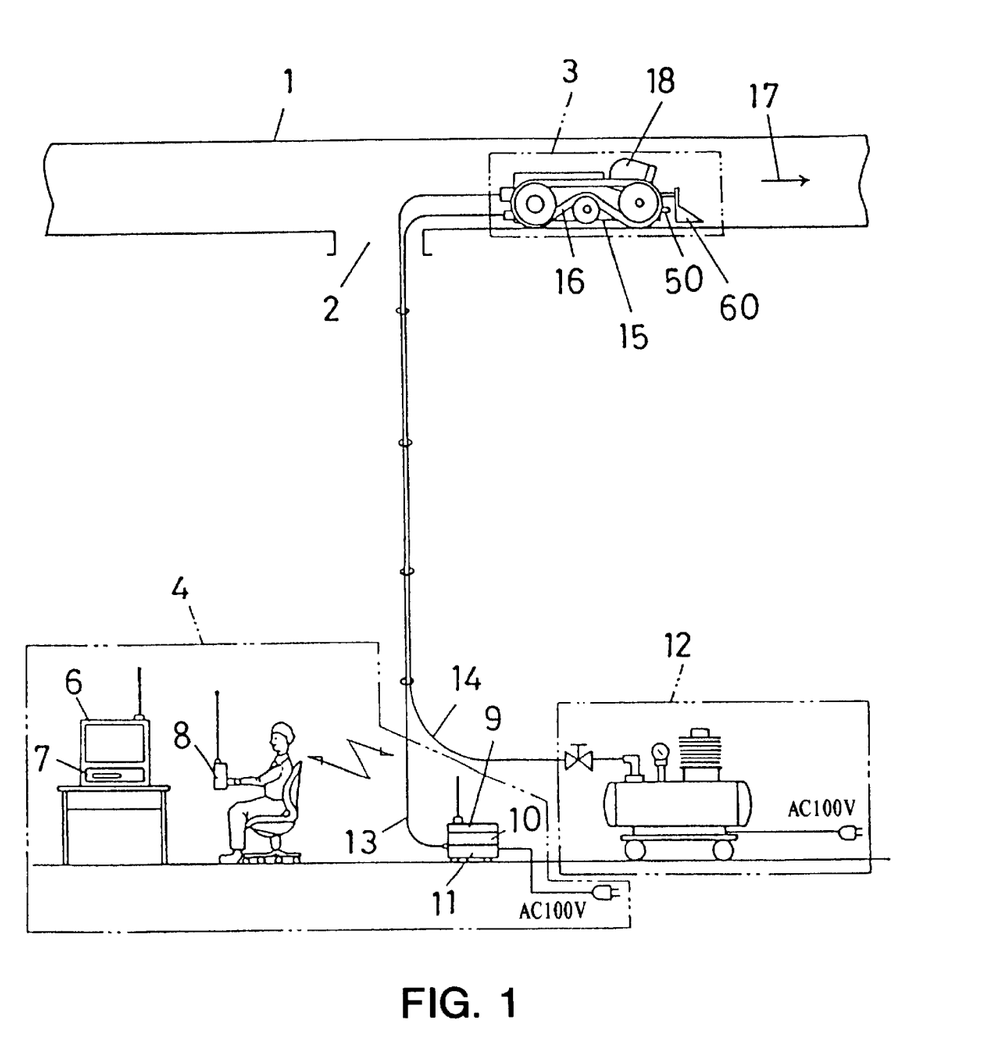
FIG. 1 shows the entire constitution of a preferable model of the apparatus for sampling dust in a duct in accordance with the invention.

In FIG. 1 reference number 1 stands for a duct, 2 for an equipment admittance orifice provided in the duct 1, 3 for a traveling portion admitted through the equipment orifice 2, 4 for a remote control portion, and 12 for a compressor portion for generating compressed air.

The traveling portion 3 is retrievably inserted into the duct 1 through the equipment admittance orifice 2. The traveling portion 3 comprises a traveling truck 15 which carries a TV camera (described later), bucket means 60, compressed air ejection nozzles 50 and an illuminating light 18, said traveling truck 15 being freely movable forwardly and backwardly in the duct 1. Reference number 16 represents power-transmission round belt(s) connecting wheels of the traveling truck 15.

The previously mentioned remote control portion 4 contains a television 6 for displaying an image taken by the TV camera 5, a VTR 7, a remote control switch 8, a transceiver 9, an amplifier 10 and a power source equipment 11. The power source equipment 11, which is power-supplied normally from AC 100V-line, has also a battery built in so as to be kept energized for 5 hours without AC 100V-supply.

The above traveling portion 3 is connected with the remote control portion 4 through a signal line 13, and with the compressor portion 12 through an air tube 14.

Reference number 17 shows a direction in which the traveling portion 3 made up of the traveling truck 15 and its on-board carrying constituents travels in the duct 1.

Figure 2:
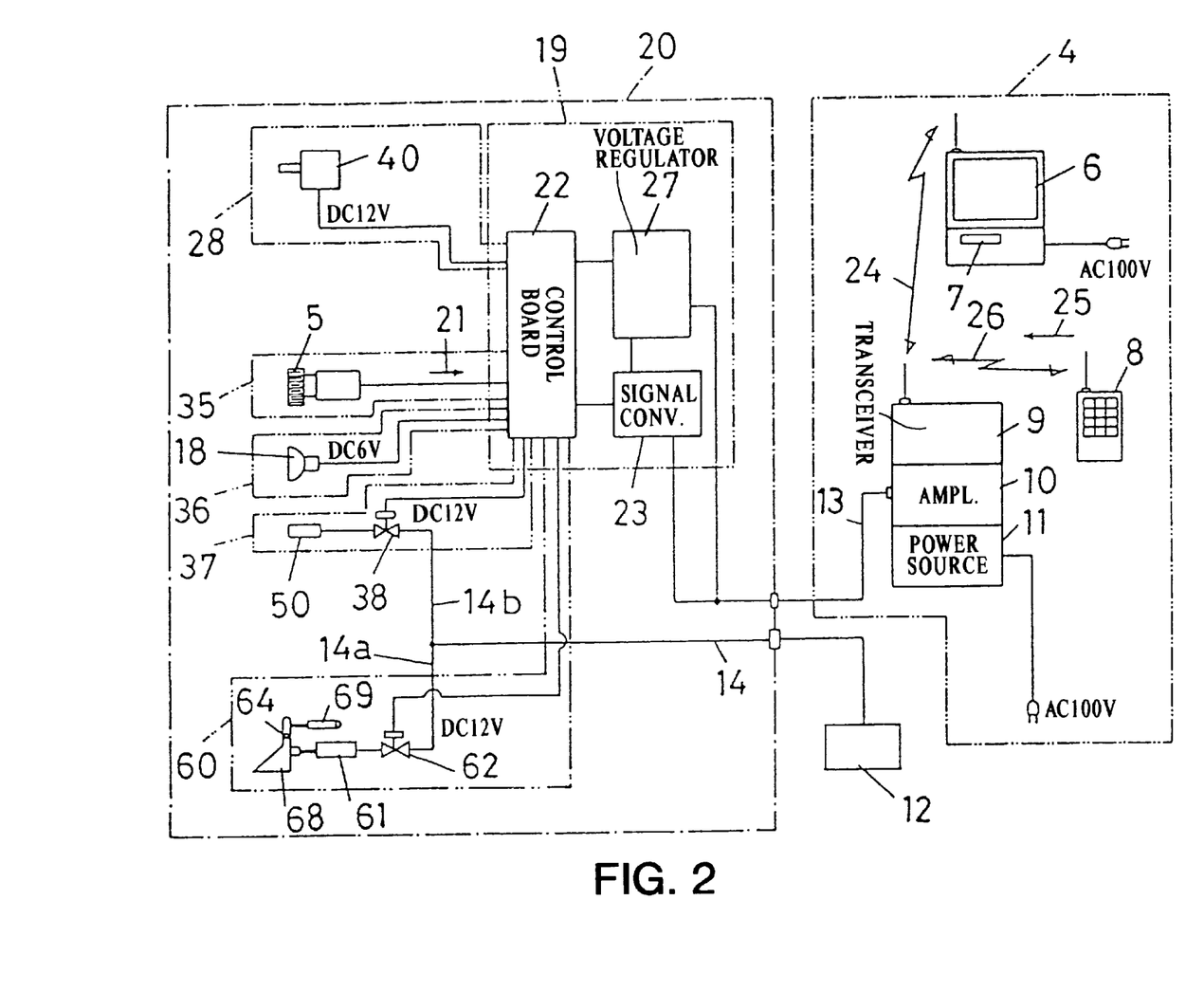
FIG. 2 is a block diagram which shows the traveling portion control device mounted on the traveling portion and the remote control portion remotely connected to the traveling portion control device.

Next the control mechanism of the apparatus is described according to FIG. 2. The traveling portion 3 is provied with a traveling portion control device 20 having its core part 19 composed of a control board 22, a signal converter 23 and a voltage regulator 27. The control board 22 is connected to a traveling system 28, a TV camera system 35, an illuminating light system 37 and a bucket means system 60. The previously mentioned transceiver 9 forms the pivotal part of the remote control portion 4, which remotely exchanges signals with the traveling portion control device 20 through the signal line 13; the transceiver receives, through the control board 22 and the signal converter 23 both in the core part 19, the signal 21 outputted from the TV camera 5 in the TV camera system 35, and then transmits the signal 21 to the television 6 and the VCR 7 by means of electromagnetic waves 24 in the remote control portion 4. The scene in front of the traveling portion 3 (including the foreign matter heaped in and sticking to the duct 1) is taken by the TV camera 5 and then displayed on the television 6 and recorded in the VCR 7. On the other hand an operator of this apparatus manipulates a remote control switch 8 to send operation signals 25 in the form of electromagnetic waves 26 to the transceiver 9 in accordance with an image displayed on the television 6. The operation signals 25 received by the transceiver 9 are transmitted to the control board 22 through the signal line 13 and the signal converter 23 contained in the the traveling portion control device 20. The control board 22 makes the received signals control the previously mentioned systems 28, 35, 36, 37 and 60.

The above voltage regulator 27 supplies a voltage suitable for the electric equipment in each of the systems 28, 35, 36, 37 and 60.

The traveling system 28 contains an electric motor 40, which is supplied, for instance, with DC 12V.

The TV camera system 35 contains the TV camera 5.

The illuminating light system 36 contains the illuminating light 18, which is supplied, for instance, with DC 6V.

The ejection nozzle system 37 contains the compressed air ejection nozzle 55 and the magnetic valve 38 for allowing and stopping the flow of the compressed air supplied from the compressor portion 12 through the air tube 14. The electromagnetic check valve 38 is supplied, for instace, with DC 12V.

The bucket means system 60 contains an air cylinder 61 and an electromagnetic valve 62 for allowing and stopping the flow of the compressed air supplied to this system 60 from the compressor portion 12 through the air tube 14. The electromagnetic valve 62 is supplied, for instance, with DC 12V.

The traveling portion 3 has its constitution described in further detail in the following in accordance with FIG. 3 to FIG. 7.

Figure 3:
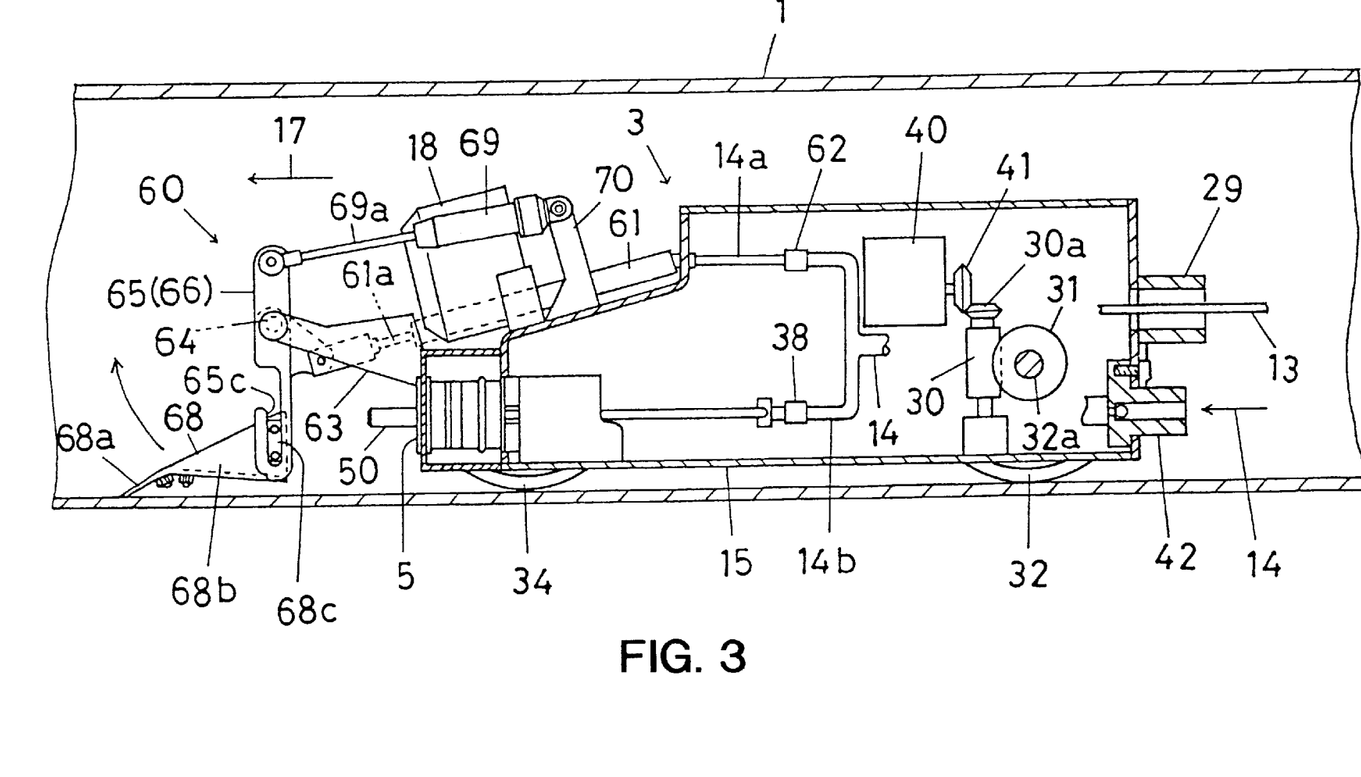
FIG. 3 shows a partial cross-sectional side view of the traveling portion.
Figure 4:
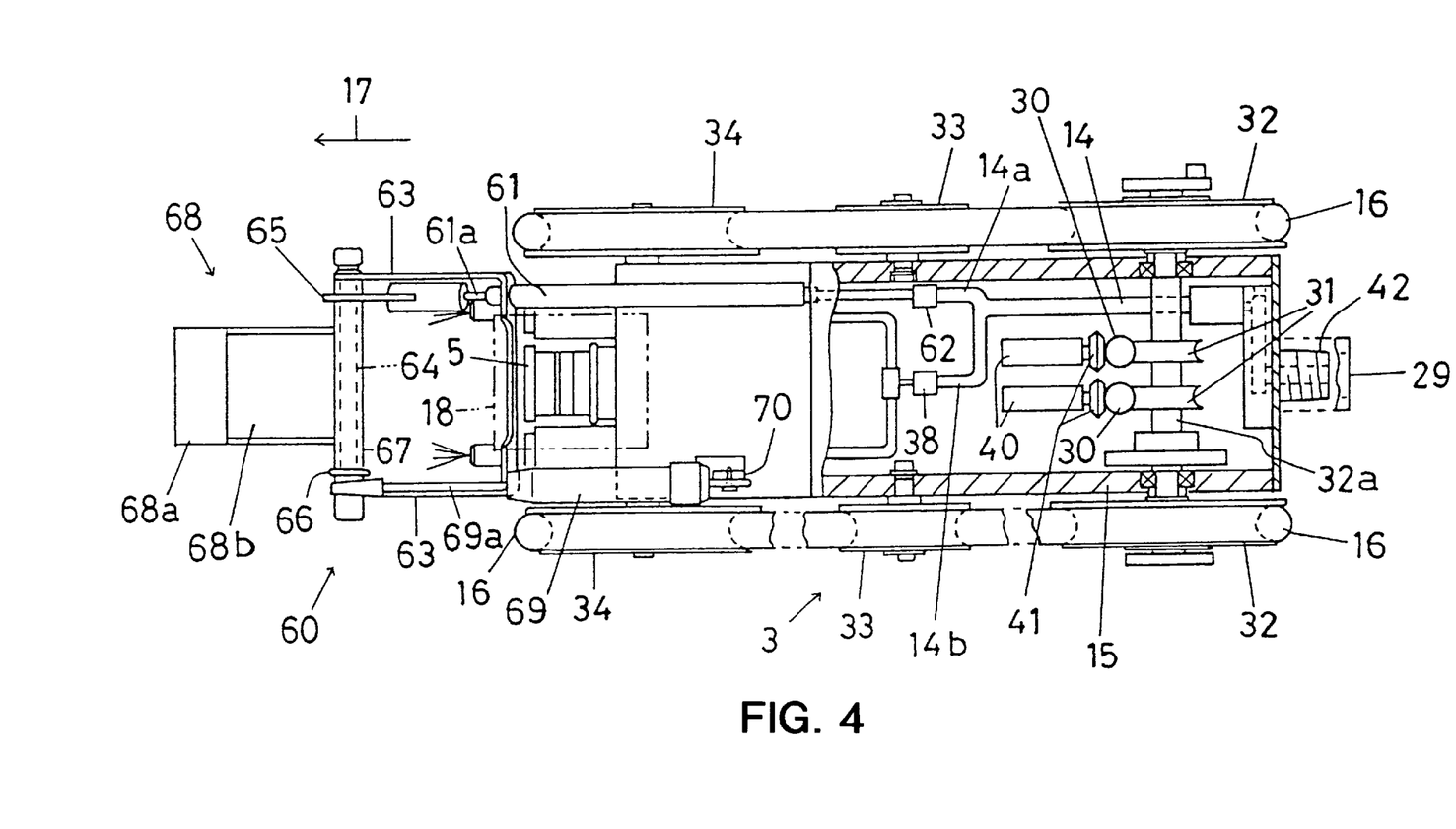
FIG. 4 shows a partial cross-sectional plan view of the traveling portion.

The traveling truck 15 of the traveling portion 3 has its back side provided with an electric socket 29 for connecting the signal line 13 thereto and with an air socket 42 for connecting the air tube 14 thereto.

Futher the traveling truck 15 has on both sides a pair of driving wheels 32 in the backward section, a pair of trailing wheels 34 in the forward section and a pair of guide rollers 33 in the middle section. These wheels and rollers on each side are linked mutually by means of a belt to transmit a driving force from the driving wheel 32 to the trailing wheel 34 through the guide roller 33. As a mechanism to drive the driving wheel 32, there are provided on the driving truck 15 the previously mentioned electric motor 40, a miter gear 41 attached to the shaft of the motor 40, another miter gear 30a engaged with the miter gear 40 and having its shaft provided oppositely with a worm gear 30, and a worm wheel 31 meshing with the worm gear 30 and having its shaft made common with the shaft 32a of the driving wheel 32. A similar driving mechanism is provided also to the other of the pair of driving wheels 32 so that the two driving wheels 32 can independently operated. Thus the traveling truck 15 is made, through the operation of the remote control swich 8, not only to progress, retrogress and stop but also to turn to the right and left.

Figure 5:
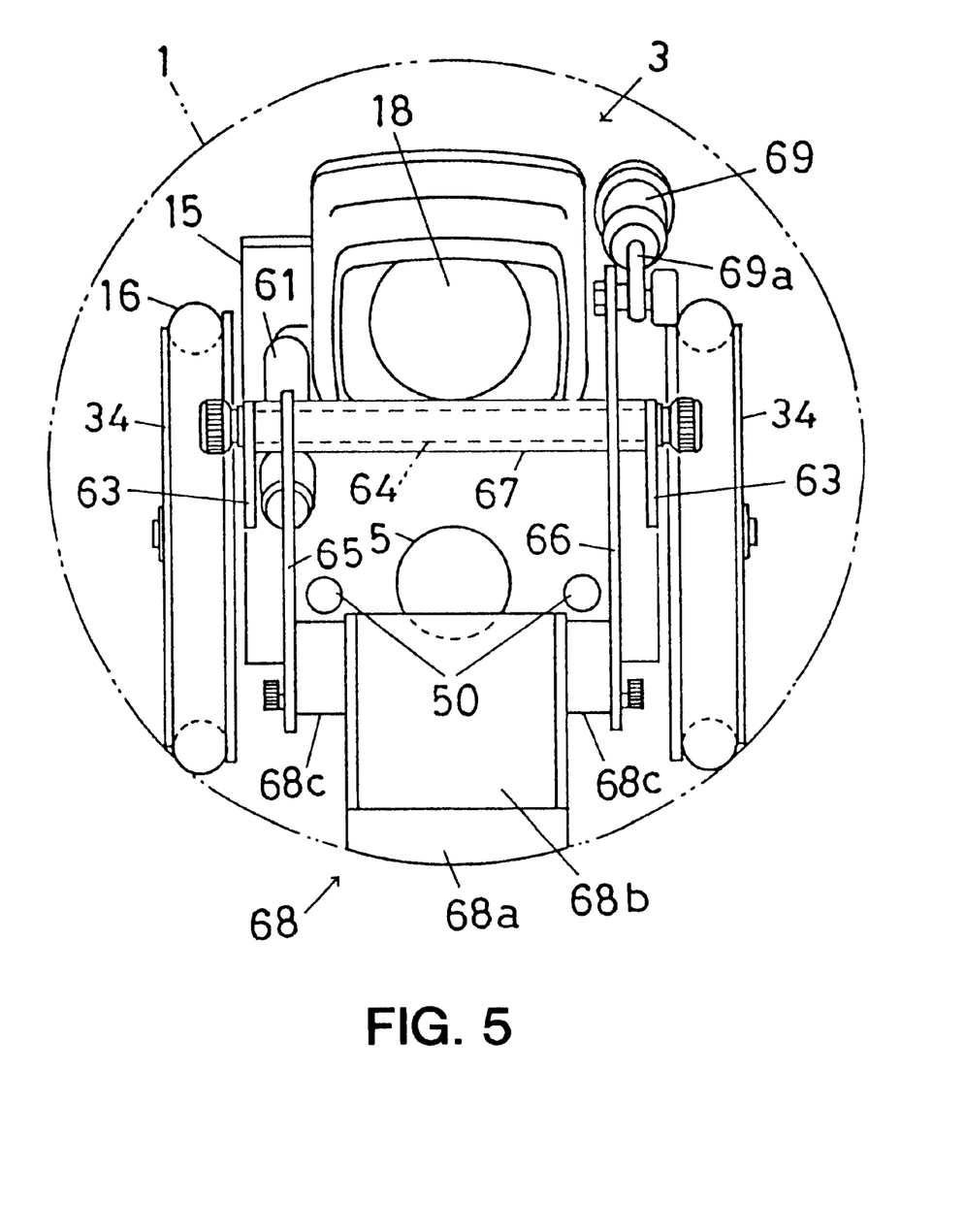
FIG. 5 show the front view of the traveling portion.

The previously mentioned TV camera 5 is positioned at the lower central part of the forefront of the traveling truck 15, observing the forward scene in the duct 1.

The previously mentioned pair of compressed air ejection nozzles 50 are arranged on both sides of the TV camera 5 and fixed so as to eject compressed air forward obliquely downward.

The previously mentioned illuminating light 18 is located at the forward upper central position of the traveling truck 15 and directed forward obliquely downward.

In this model of the present invention the TV camera 5, the illuminating light 18 and the compressed air ejection nozzles 50 for allowing and stopping compressed air ejection have their on-and-off operation controlled through the control board 22 by the remote control switch 8, with their respective viewing, illuminating and air-ejecting directions fixed. However, this model may be modified so that the remote control portion 4 controls also the illuminating direction of the illuminating light 18 and the air-ejecting direction of the compressed air ejection nozzles 50.

Figure 6:
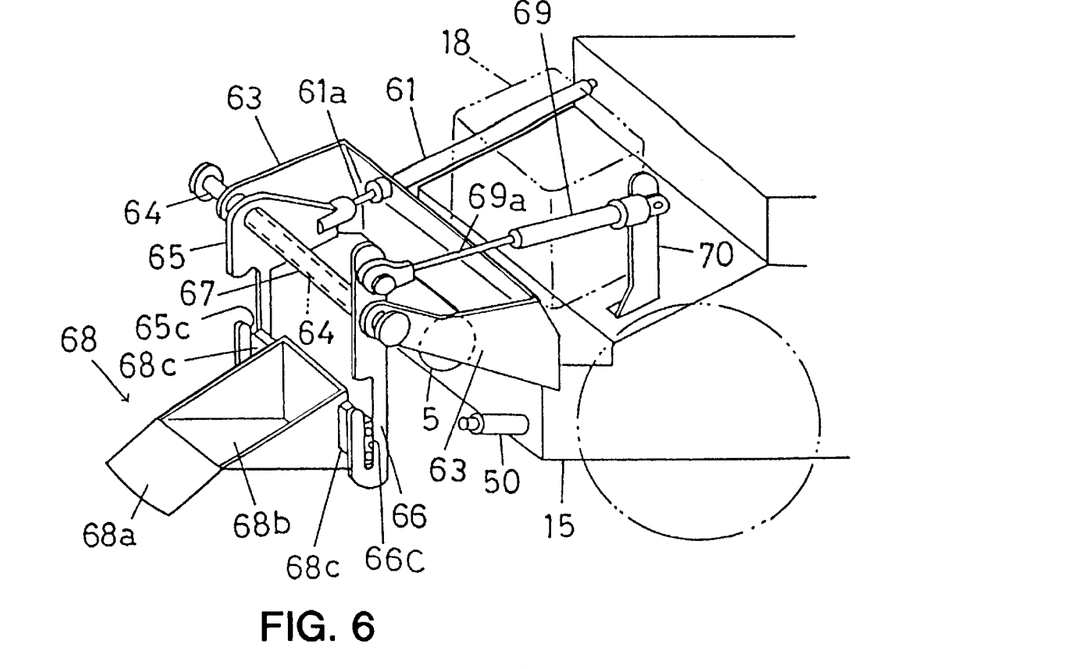
FIG. 6 shows a perspective view of bucket means of the traveling portion.

The previously mentioned bucket mean s 60 is attached to the forward end of the traveling truck 15; the traveling truck 15 is provided at its forward end with a pair of supporting elements 63 extending forward to support therebetween a shaft 64, and a pair of rotation arms 65, 66 is supported by the shaft 64 rotatably around the same, and then a sampling bucket 68 is detachably attached between said pair of rotating arms 65 and 66 to complete the previously mentioned bucket means 60. The pair of rotation arms 65, 66 are fixed respectively to both ends of a hollow cylindrical member 67 which rotatably sourrouds said shaft 64. Both the rotation arms 65 and 66 can thus turn around the shaft 64 as an integrated one body.

One of the pair of rotation arms 65, 66, namely the arm 65, is connected to the rod 61a of the previously mentioned air cylinder 61, while the other of the pair of rotation arms 65, 66, namely the arm 66, is connected to the rod 69a of the previously mentioned hydraulic damper 69. The footing end of the air cylinder 61 is fixed to a part of the frame of the traveling truck 15, while the hydraulic damper 69 has its footing end pivotally supported by a fixing pillar 70 supported on the frame of the traveling truck 15.

The air cylinder 61 has its rod 61a forced by a spring provided in the cylinder 61 normally in the receding direction so that the rod 61a is kept at the most recessed position while the air cylinder 61 is not supplied with pressing air. To the contrary, while the air cylinder 61 is kept supplied with pressing air, the rod 61a proceeds to the most advanced position resisting the above mentioned spring in the cylinder 61. Thus the rotation arms 65, 66 turn through an angle corresponding to the movement of the rod 61a of the air cylinder 61 between the above mentioned most recessed and most advanced positions.

The previously mentioned hydraulic damper 69 is to moderate the sudden movement of the rod 61a arising at an instance when pressing air is introduced to, stopped or released from the air cylinder 61. Therefore, by connecting the hydraulic damper 69 to the rotating arm 66, the sudden turning of the rotation arms 65, 66 due to the air cylinder 61 is relaxed, and their turning become smooth. Therefore, the sampling bucket 68 attached to the pair of rotating arms 65 and 66 is made to turn smoothly.

When the air cylinder 61 has its rod 61a kept at the most recessed position, the rotation arms 65, 66 are set nearly vertical causing the sampling bucket 68 to be kept at the lowest position. This lowest position of the bucket is the scooping position for scooping dust accumulations in the duct 1.

In the above scooping position the hydraulic cylinder 69 has its rod 69a kept in the most advanced position, and the rotation arms 65, 66 are prevented from turning further. On the other hand the air cylinder 61 has, in this scooping position, its rod 61a kept in the most recessed position, and the rotating arms 65, 66 are prevented from turning further also in this case. Namely, in the scooping position of the sampling bucket 68 the air cylinder is prevented from receding further.

By making the traveling truck 15 proceed with the sampling bucket 68 kept in the scooping position, the bucket 68 scoops foreign matters accumulated in the duct 1 for sampling.

With pressing air introduced into the air cylinder 61, the rod 61*a* proceeds from the most recessed position opposing the spring, pushes the rotation arm 65 and makes the rotation arms 65, 66 turn clockwise from the vertical position as shown in FIGS. 3 and 6. The sampling bucket 68 fixed to the rotation arms 65, 66 thus turns leaving from the scooping position and finally reaches the standby position when the rod 61*a* further proceeds to the most advanced position. The standby position is apart from the lowest-kept scooping position by an angle not exceeding 90°. This standby position corresponds to the most recessed position of the rod 61*a* of the air cylinder 61, and therefore, the sampling bucket 68 is prevented from turning further. The standby position should be chosen as a position where the sampling bucket 68 does not touch the bottom of the duct 1 and the scooped dust sample does not spill easily. At the same time the standby position is experimentally confirmed so as not to obstruct the visual field of the TV camera 5.

Figure 7A:
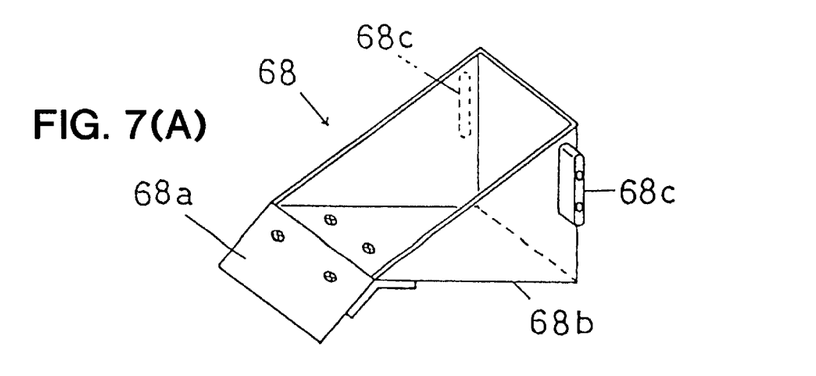
Figure 7B:
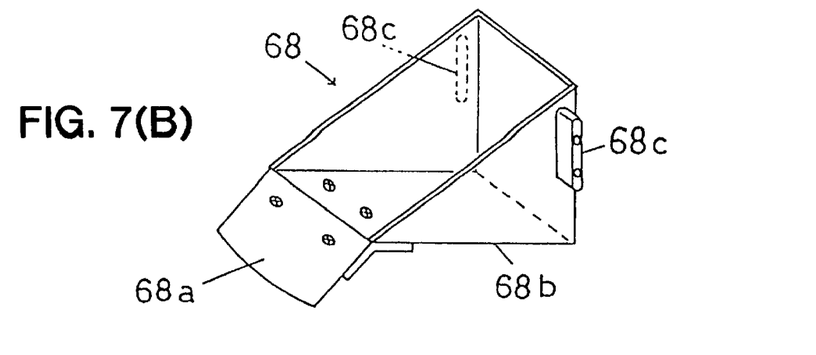

Next the constitution of the sampling bucket 68 is described together with the constitutional relationship between the sampling bucket 68 and rotation arms 65, 66. The sampling bucket 68, which is to scoop accumulations in the duct 1, is detachably attached to the rotation arms 65, 66. The sampling bucket 68 shown in FIG. 7(A) is suitable for a duct having a flat bottom, and the scooping plate 68*a* attached to the bucket body portion 68*b* has its lower edge made linear. The sampling bucket 68 shown in 7(B) is to be used in a cylindrical duct, and the scooping plate 68*a* has its lower edge made curved so as to fit the curvature of the duct. The bucket body portion 68*b* of the sampling bucket 68 has triangular side walls, and the inclined faces following the scooping plate 68*a* are made open upwards from the front. The accumulations scooped up from the duct through the scooping plate 68*a* are, as they are, introduced into the bucket body portion 68*b*. The bucket body portion 68*b* is provided on both outer sidewalls with keys 68*c* for interlocking with key slots 65*c*, 66*c* provided on the rotating arms 65, 66. The key slots 65*c*, 66*c* of the rotating arms 65, 66 are made longer than the keys 68*c* so that the sampling bucket 68 interlocked in the key slots 65*c*, 66*c* can move vertically along the possible unevenness of the bottom surface of the duct 1. The sampling bucket 68 is thus enabled to proceed in the duct always kept in touch with the bottom surface of the duct 1.

In addition the bucket body portion 68*b* of the sampling bucket 68 is made of transparent plastic resin for the purpose of enabling the TV camera 5 to catch the forward scene through the transparent bucket body portion 68*b* even if the sampling bucket 68 is kept at the scooping position. Further the scooping plate 68*a*, which may be of plastic, can be made replaceable, since the scooping plate 68*a* not only wears and tears but also must be made different in shape in accordance with the shape of the duct 1, the feature of accumulations to be sampled and the state of accumulation. The touching angle of the scooping plate 68*a* to the duct bottom is adjusted by adjustig the attaching angle to the bucket body portion 68*b*.

Referring to FIGS. 3 and 4, it is understood that the pressing air supplied to the air cylinder 61 is in common with the compressed air to be supplied to the compressed air ejection nozzles 50. The air tube 14 is led to the traveling truck 15 through the air socket 42. The air tube 14 led to the traveling truck 15 branches out to an air tube 14*a* toward the air cylinder 61 and an air tube 14*b* toward the compressed air ejection nozzles 50. The tubes 14*a* and 14*b* have electromagnetic valves 62 and 38, respectively on the air cylinder side and on the nozzle side. These valves 62 and 38 are on-and-off controlled through the control board 22 by the remote control switch 8.

Operation of the apparatus is described in the following. With the sampling bucket 68 attached to the pair of rotation arms 65, 66 by means of interlocking, the traveling truck 15 is inserted into the duct 1 through the equipment admittance orifice 2. After switching on the illuminating light 18 and the TV camera 5 by operating the remote control switch 8, the traveling truck 15 is made to start by making the electric motor 40 energized through the operation of the remote control switch 8. At this time the sampling bucket 68 is kept in the upward standby position by introducing compressed air into the air cylinder 61 to make the rod 61*a* proceed to the most advanced position. Introduction of the compressed air is realized by making the electomagnetic valve 61 open through the operation of the remote control switch 8.

While the traveling truck 15 is traveling, the TV camera 5 transmits the scene in front of the traveling truck 15 to the television 6 and the VCR 7. The operator of the apparatus can observe the state of dust accumulation in the duct 1 by watching the television 6. Watching the television 6, the operator makes the sampling bucket 68 turn to the scooping position from the standby position with the the traveling truck 15 stopped or kept traveling, when the traveling truck 15 comes to a predetermined position or to the place where the operator considers that sampling is necessary. The sampling bucket 68 is made to turn to the scooping position from the standby position by the spring force pushing back the rod 61*a* with the air cylinder 61 kept not supplied with pressing air by closing the electromagnetic valve 62. All the above operation is of course realized through the operation of the remote control switch 8.

With the traveling truck 15 kept traveling forwardly after the sampling bucket 68 is made to turn to the scooping position from the standing position, the bucket 68 in touch with the bottom of the duct 1 scoops accumulations in the duct 1.

Further it is possible, as an occasion demands, to make the pair of comprssed air ejection nozzles 50 eject compressed air toward the accumulations, before lowering the bucket to the scooping position by opening the electromagnetic valve 38 in the path of the air tube 14*b* leading to the compressed air ejection nozzles 50. Compressed air ejection from the nozzles 50 causes such a situation change in the duct 1 as the foreign matter accumulations are partially or fully blown off leaving contaminations sticking to the duct 1. The process of situation change and after-blow state in the duct 1 are displayed on the television 6 and recorded in the VCR 7. Kinds, properties and the state of sticking of remaining contaminations are thus made clear. Contaminations left in the duct 1 without being blown off can be further sampled by the sampling bucket 68.

After the sampling by means of the sampling bucket 68 is completed, the traveling truck 15 is returned to the equipment admittance orifice 2 with the sampling bucket 68 turned back to the standby position, and then the bucket 68 is taken out for analysing the sample.

Further the present invention can be used only for cleaning a duct by blowing off the accumulations in the duct by means of the pair of compressed air ejection nozzles 50 while the traveling truck 15 is made to travel in the duct with the sampling bucket 68 detached. It is, of course, obvious that the present invention is used also to confirm the cleaning effect after the completion of duct cleaning.

INDUSTRIAL APPLICATION

As is understood from the above description, the apparatus for sampling dust in a duct in accordance with the present invention can be used in such a narrow duct as can not be accessed internally by a person, to collect samples necessary, to know the kinds of matters accumulated in the duct, the state of accumulation and sticking or the like. The apparatus according to the present invention can be applied to various ducts, particularly narrow ducts, used in various fields of industry.

The foregoing relates to a preferred exemplary embodiment of the invention, it being understood that other variants and embodiments therefore are possible within the spirit and scope of the invention, the latter being defined by the appended claims.

We claim:

1. An apparatus for sampling dust in a duct, comprising:
   a traveling truck (15) capable of traveling forwardly and backwardly in the duct (1);
   an illuminating light (18) mounted on a front side of said traveling truck for illuminating an inside of said duct;
   a TV camera (5) mounted on said front side of said traveling truck (15) for observing an inside surface of said duct (1);
   at least one compressed air ejection nozzle (50) mounted on said front side of said traveling truck for ejecting compressed air toward accumulations in front of said traveling truck;
   a sampling bucket means (68) attached to a front of said traveling truck (15) for sampling accumulations in said duct (1);
   said sampling bucket means (68) comprising:
      a shaft (64) supported by and between a pair of supporting elements (63) projecting from the front side of said traveling truck (15);
      a pair of rotation arms (65, 66) rotatably around said shaft (64);
      at least one air cylinder (61) for rotating said pair of rotation arms (65, 66) between a standby position and a scooping position;
      a hydraulic damper (69) for deadening a turning speed of said rotation arms (65, 66) made to turn by said air cylinder (61);
   said sampling bucket means (68) is detachably attached between said pair of rotation arms (65, 66); and
   a remote control portion (4) for remote control of said traveling truck (15), said illuminating light (18), said TV camera (5), said at least one compressed air rejection nozzle, and said bucket means (68).

* * * * *